United States Patent [19]

Crosby

[11] Patent Number: 5,037,405
[45] Date of Patent: Aug. 6, 1991

[54] INTRAVENOUS TUBING CONNECTOR LOCK

[76] Inventor: Sue A. Crosby, 2299 NW. 21st Pl., Gainesville, Fla. 32605

[21] Appl. No.: 475,921

[22] Filed: Feb. 6, 1990

[51] Int. Cl.⁵ .......................................... A61M 25/00
[52] U.S. Cl. ................................................. 604/283
[58] Field of Search .............. 604/283, 175, 177, 240, 604/243, 905

[56] References Cited

U.S. PATENT DOCUMENTS

| | | | |
|---|---|---|---|
| 2,763,266 | 9/1956 | Evans | 604/283 |
| 4,006,744 | 2/1977 | Steer | 604/283 |
| 4,191,185 | 3/1980 | Lemieux | 604/283 |
| 4,429,852 | 2/1984 | Tersteegen et al. | 604/283 |
| 4,473,369 | 9/1984 | Lueders et al. | 604/283 |
| 4,610,670 | 9/1986 | Spencer | 604/905 |
| 4,723,948 | 2/1988 | Clark et al. | 604/283 |
| 4,801,296 | 1/1989 | Vaillancourt | 604/905 |

FOREIGN PATENT DOCUMENTS

| | | | |
|---|---|---|---|
| 0183396 | 6/1986 | European Pat. Off. | 604/283 |
| 2578746 | 9/1986 | France | 604/283 |

OTHER PUBLICATIONS

Smith et al., "A Safer Coupling Collar for the Catheron Linkages" British J. of Radiology, 50, 592-593, 1977.

Primary Examiner—C. Fred Rosenbaum
Assistant Examiner—Sharon Finkel

[57] ABSTRACT

An enclosure with two hinged clamping members (1 and 2) with finger-like prongs on each identical end is provided for holding together the end components (4, 5, 6, 7 and 10) of a multiple intravenous (I.V.) needle and tubing flange set-up. The end components may be either a plastic hub, a needle through the rubber stopper of the side infusion port of the main IV line, the terminal portion of an IV extension set or the connector site of the IV line to the actual IV catheter. When an I.V. needle and tube are connected and the enclosure is open, the connected parts can be placed therein and then locking members (16) are snapped together to hold the components securely connected. Convenient snap-locking can be utilized to hold the locking members (16) together. A use method includes inserting a needle (4) into a flange cap (10) and then placing the joined components into the enclosure, locking the locking members (16) shut and then opening them for changes and alterations as necessary.

6 Claims, 1 Drawing Sheet

INTRAVENOUS TUBING CONNECTOR LOCK

BACKGROUND OF THE INVENTION

This invention relates to medical intravenous needles and medical tubing connections and more particularly to securing connection of intravenous (I.V.) needles for transferring prescription fluid from one or more intravenous bags to a main tubing line for injection into patients.

The most common current method for securing connection of transfer intravenous (I.V.) needles from prescription-bag tubing to main intravenous tubing is to tape them together, tape being such a common item in medical conditions. Use of tape is very unreliable since the tape often loses its hold and the I.V. tubing becomes disconnected. Also, both applying and removing the tape is messy and very time consuming. Furthermore, the tape may be a source of infection for the patient should it become damp or contaminated. Most problematic, however, is danger of needle sticking and the spread of disease, particularly AIDS and other contagious infections. A variety of devices have been developed in an attempt to alleviate these potential problems.

One referenced on page 50 of the May, 1989 issue of the "NURSING 89" magazine features an enclosed needle and a locking device referred to as the "Click Lock " I.V. system. Another is referred to under the trademark name of "Needle Lock. " Both of these are advantageous over the present use of tape, but neither is compatible with existing medical tubing connections and both are relatively expensive. Even another device sold under the name "Line-Gard " is a one-time use device which does not allow for easy sequential line removal and replacement.

Danger of needle-sticking injury to health care practitioners and related cost problems occur frequently from repetitious handling of needles that do not stay connected to tubing flanges and that contaminate tape when they are disconnected. When a needle is connected to a tubing flange, there need not be blood or other prescription fluid in the needle. Flow can be initiated after connection has been achieved and secured with this invention, thus preventing contact with prescription fluids passing through the needle connection.

Prior U.S. patents for securing connection of tubular-shaped objects have been found in the technical area of electrical-cord connector housings. These have never been employed in the medical field because they have been devised and formed particularly for the electrical field. While there is some similarity in the physical problem involved, there are great differences in the structure and relationship of parts. No patents and no prior art other than that mentioned above has been found in this field.

The prior U.S. patents found in the field of housings or locks for electrical-cord connections including the following:
4,643,505 House, 1987
4,169,643 Gallager, 1979
4,143,934 Siebert, 1979
4,049,357 Hamisch, 1977
3,499,102 Gillemot et al., 1970
3,344,393 Hendee, 1965
3,191,600 Everett, 1962
3,059,209 Bird, 1962.

Exemplary of these patents is the first listed patent, 4,643,505. It features methods of adapting wire and connector sizes. The differences in all of these patents relate primarily to adapting to the characteristics of electrical plugs. The difference with this invention is that it relates to characteristics for securing the connection of medical tubing by transfer needles. Thus, these prior patented devices would not be usable to connect medical tubing.

SUMMARY OF THE INVENTION

A major object of this invention is to provide a reliable, convenient, sanitary and low-cost method for securing the connections of an I.V. infusion set-up, including both intermittent and continuous infusion of prescription I.V. fluid and/or medication.

An ultimate objective is to eliminate accidental needle sticks and ensure correct and complete infusion of the prescribed fluid(s).

The present invention accomplishes the above and other objects by providing a lock with two clamping members hinged together and provided with one-half of a compartment for components of a connected I.V. needle and tube in each clamping member. When an I.V. needle and tube are connected and the enclosure is open, the connected parts can be placed inside and closing the clamping members together holds the parts securely connected. Convenient snap-locking can be utilized. The snap-lock clamps can be released with one hand if necessary and reused for the next infusion. Optionally, the invention may be color coded for ease of medication identification.

BRIEF DESCRIPTION OF THE DRAWINGS

A complete understanding of the invention is available by reference to the following drawings in relation to the description of preferred embodiments and claims:

DETAILED DESCRIPTION OF PREFERRED EMBODIMENTS.

Figure 1:
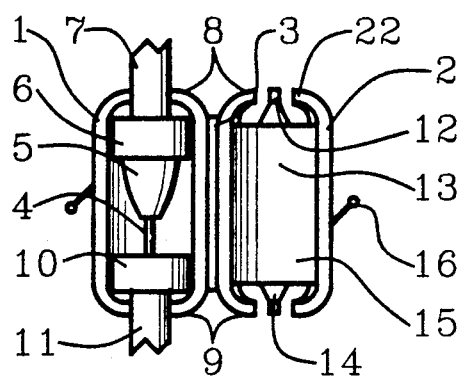
FIG. 1 is a top view of the invention in opened condition.

Referring to FIG. 1, a first clamping member 1 is hinged to a second clamping member 2 with hinge 3. The hinge 3 can be a "live " flexible material or a bolt-and-eye type and may comprise one or more spaced hinged members. Each of the two clamping members 1 and 2 is provided with hollow compartments, such as 13 and 15. In its simplest form, the compartments would be merely semi-circularly shaped hollow spaces running the length of the clamping member with no specially shaped surface. In FIG. 1, a needle 4 attached to luer 5 extending from input medical tubing flange 6 on prescription-bag tubing 7 at an input end 8 of the clamping members 1 and 2 is shown in the compartments 13 and 15. The two clamping members 1 and 2 are illustrated in an open condition in FIG. 1 with the compartments 13 and 15 vacant at one side and the matching compartments at the other side containing components of connected intravenous needle 4 and medical-tubing flange cap 10.

The compartments in each of the two clamping members 1 and 2 can be mirror images of each other or constructed to provide a compartmentalized form similar to that which would be achieved with mirror-image construction. The compartments at the input end 8 can be a semi-cylindrical inlet tubing channel 12 at each side of the clamp members 1 and 2 with the channel 12 terminating at an inlet compartment 13. The compartment at the output end 9 can be a semi-cylindrical outlet compartment 15.

All of the compartments can be constructed with a wide variety of contact surfaces to fit the size and shape of the needle 4, flanges 6 and 10, luer 5 and other medical-tubing components. In its simplest form the compartments could be merely semi-circular hollow spaces running the length of the clamping members with no specially-shaped surfaces. In this illustration, the contract surface is smooth and contoured to match the outside surfaces of the components. But the contact surfaces can be ribbed, pronged, fibrous or otherwise partial-contact nesting elements within the clamping members 1 and 2. The outside of the clamping members 1 and 2 also can be constructed with a variety of shapes which may or may not be symmetrical. Either or both clamping members 1 and 2 can be square-cornered, rounded, finger-grooved or otherwise formed for functional or aesthetic objectives.

Locking members 16 can be provided to hold the clamping members 1 and 2 together. Outward linear pulling will not cause the clamping members 1 and 2 to open and release connected tubing because ridges of the flanges 6 and 10 are retained in the flange compartments 13 and 15. As a result of flexibility of conventional medical tubing, side pressures also will not exert opening pressure on the clamping members 1 and 2. Therefore, the locking members 16 can be constructed with relatively light holding capacity. A highly convenient and inexpensive locking means is the conventional cross-clasp which is utilized typically for various types of purses and illustrated in the drawing figures. Other locking means also are anticipated within the scope of this invention.

Figure 2:
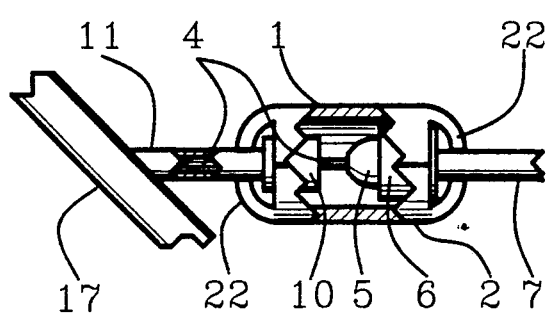
FIG. 2 is a cutaway side view.

Referring to FIG. 2, in typical use-condition, the side injection port of the input I.V. tube 11 indicated also in FIG. 1 is connected to a main I.V. tubing line 17. The clamping members 1 and 2 are illustrated in closed condition along contact line 18. Shown in cutaway sections are connected components needle 4, luer 5, input tubing 6 and rubber injection sideport 10.

The method of use is to connect the needle 4 and the injection sideport 11 initially and then to place the connected components 6 and 10 in their respective compartments 13 and 15 of one of the clamping members 1 or 2. Then the other clamping member, 1 or 2, is pivoted to a closed position over the components in the compartments and locked with locking members 16. The locking members are omitted in this illustration in order to provide a cutaway illustration of the connected components. The locking members 16 are illustrated in locked condition in FIGS. 5 and 6 and in unlocked condition in FIGS. 1 and 3.

Figure 3:
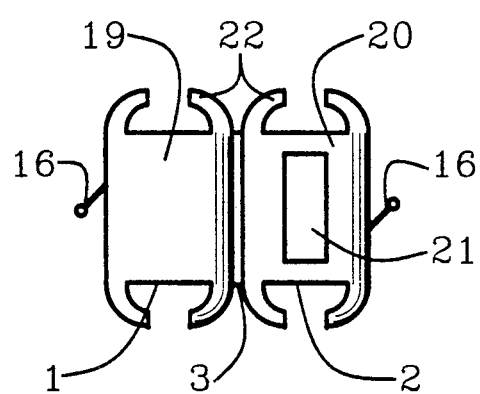
FIG. 3 is a bottom view in opened condition.

Referring to FIG. 3, outside peripheries 19 and 20 of clamping members 1 and 2 respectively are illustrated in open condition. A labeling surface 21 can be provided at either outside periphery 20 or 21 can be color-coded for different prescription fluids.

Figures 4, 5:
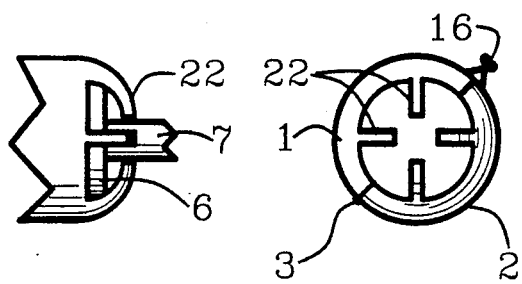
FIG. 4 is a sectional side view of a pronged end.
FIG. 5 is an end view featuring the pronged end.

Referring to FIGS. 4 and 5, end sections of the clamping members 1 and 2 can be in the form of extension or prongs 22 to secure the connecting components 6 and 10. The end view FIG. 5 shows the clamping members 1 and 2 locked together with the locking members 16 at one side and the hinge 3 at the opposite side.

Figure 6:
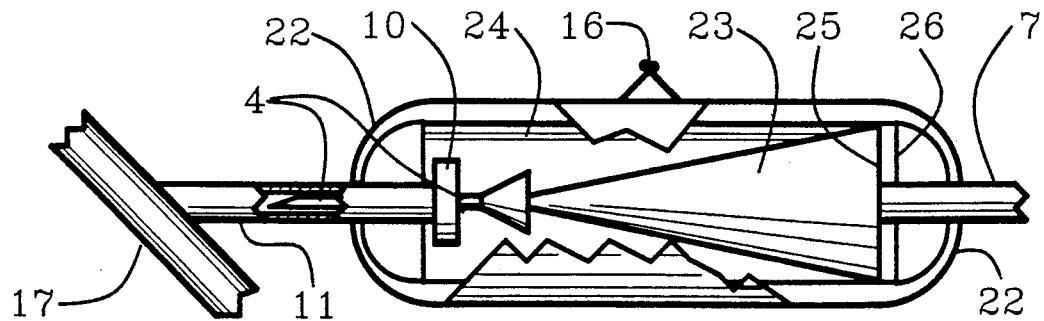
FIG. 6 is cutaway side view adapted for a particular type of I.V. needle tubing which utilizes what is known as a "flashball. "

Referring to FIG. 6, by enlarging the internal compartments 13 and 15, this same device may to contain a generally cone-shaped squeeze-bulb referred to conventionally as a "flashball" 23. Prescription-bag tubing 7 would be connected to a flashball base 25 in the flashball compartment base that would be restrained from linear movement by end prongs 22. The features of the clamping members are constructed for the size and shape of particular types of I.V. administration sets.

It will be apparent to one skilled in the art that a variety of forms, modifications and adaptations of this invention are included in the following claims.

Having thus described my invention, I claim:

1. A selectively resilient intravenous tubing connector lock comprising:
   two clamping members pivotally hinged together axially at the outside periphery of each clamping member;
   an internal hollow portion of each clamping member forming a compartment to receive the two connecting portions of any continuous or intermittent intravenous infusion set up including the Flashball device;
   identical prongs on each interchangeable end of each clamping members to receive and retain the tubing distal to each of the actual connecting sites;
   interlocking portions of a locking device positioned at the outside edges of each clamping member to interlock the two members in a closed position.

2. An intravenous tubing connector lock according to claim 1 wherein the two clamping members are constructed of selectively resilient material and joined together with a hinge component from each clamping member.

3. An intravenous tubing connector lock according to claim 1 comprised of at least two prongs on each identical end of both clamping members providing a means to grasp, stabilize, and secure intravenous tubing to an intended connecting port.

4. An intravenous tubing connector lock according to claim 1 having a flat indentation on either of the clamping members as means to provide an area for a written identification label regarding the intravenous fluid content.

5. An intravenous tubing connector lock according to claim 1 wherein the clamping members are color-coded, if desired, for identification purposes.

6. A method for using an intravenous tubing connector lock consisting of two semi-cylindrical clamping members pivotally hinged together axially at the outside periphery of each; prongs on each identical end of both clamping members providing a universal means to grasp stabilize and secure intravenous tubing to an intended injection port; a hollow internal portion formed by the closure of the clamping members to physically protect the actual site of connection and interlocking portions of a locking device positioned at the outside edge of each clamping member which when interlocked, will secure the two clamping members in a closed position until released.

* * * * *